United States Patent [19]

Scott

[11] 4,350,151
[45] Sep. 21, 1982

[54] EXPANDING DILATOR

[75] Inventor: F. Brantley Scott, Houston, Tex.

[73] Assignee: Lone Star Medical Products, Inc., Houston, Tex.

[21] Appl. No.: 242,720

[22] Filed: Mar. 12, 1981

[51] Int. Cl.$^3$ .......................... A61B 1/32; A61M 3/00
[52] U.S. Cl. ..................................... 128/17; 128/244; 128/345
[58] Field of Search ...................... 128/17, 4, 242–244, 128/341–343, 345, DIG. 26, 214.4, 303.19, 303.15, 303.11

[56] References Cited

U.S. PATENT DOCUMENTS

| 668,879 | 2/1901 | Miller | 128/345 X |
|---|---|---|---|
| 3,502,328 | 3/1970 | Hamilton | 128/345 X |
| 3,938,504 | 2/1976 | Dickinson et al. | 128/343 X |
| 4,168,709 | 9/1979 | Bentoy | 128/345 |

FOREIGN PATENT DOCUMENTS 795316 5/1958 United Kingdom ................ 128/343

*Primary Examiner*—Stephen C. Pellegrino

[57] ABSTRACT

A dilator for use in implant and other types of urologic surgery which reduces tissue abrasion and damage includes radially separable longitudinal sections for variably dilating generally cylindrial urinary passages and tissue formations. The controlled variable dilation is accomplished by inserting a generally wedge-shaped member between the radially separable sections until the proper degree of dilation has been achieved. The wedge-shaped member can carry an instrument such as a needle and suture through the dilated body passage.

4 Claims, 9 Drawing Figures

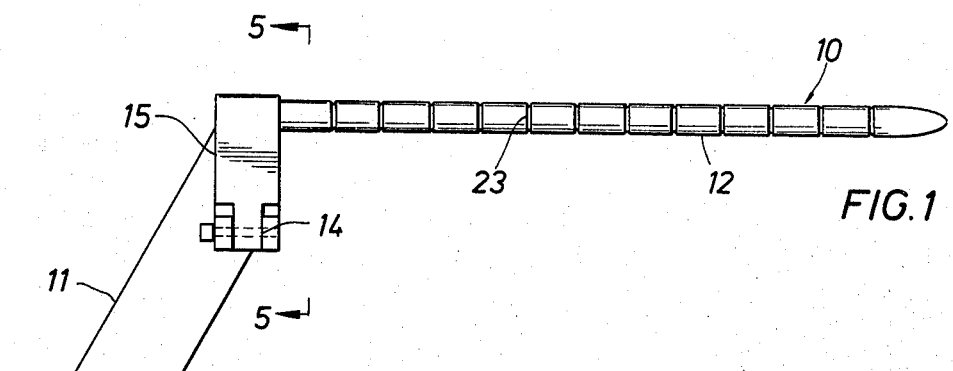
FIG. 1
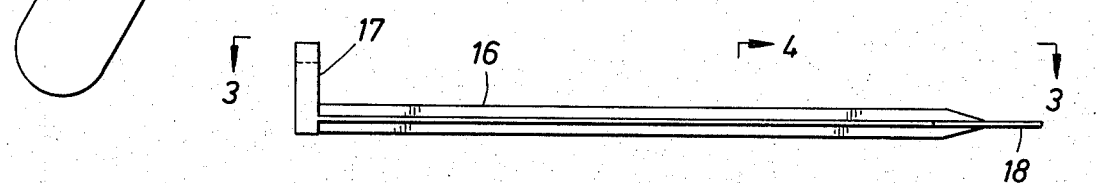
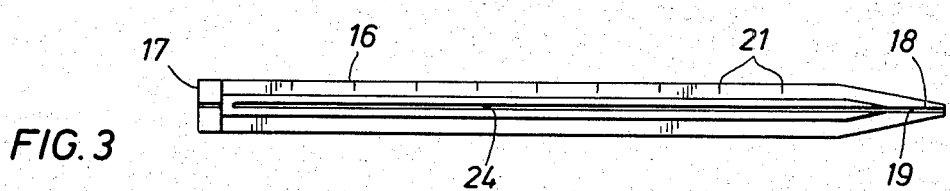
FIG. 3
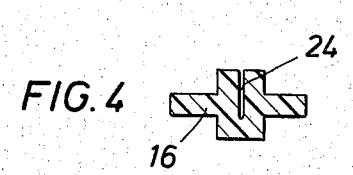
FIG. 4
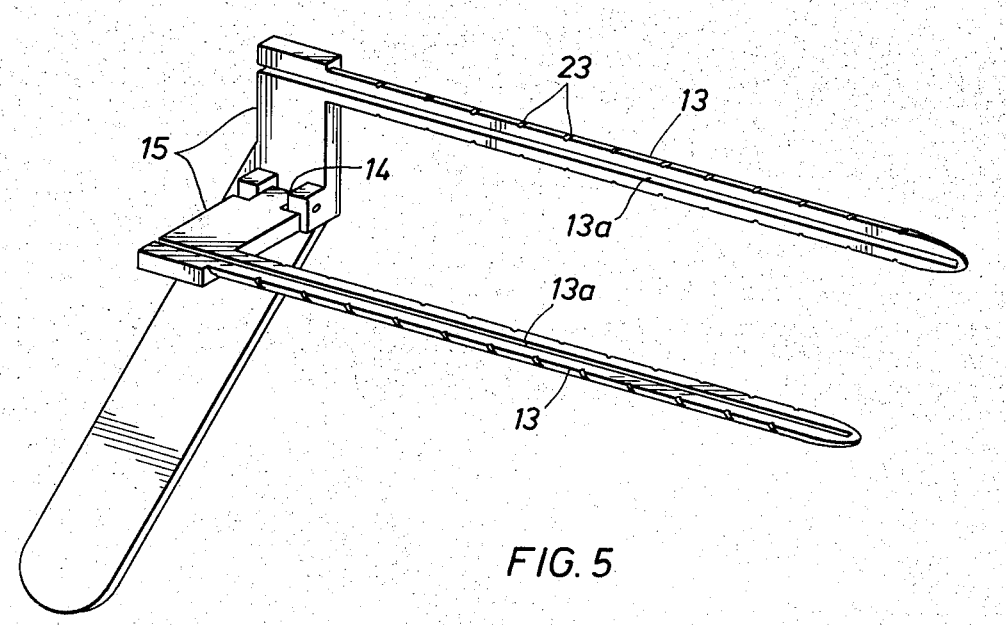
FIG. 5

EXPANDING DILATOR

BACKGROUND OF THE INVENTION

A. Field of the Invention

This invention relates to dilators for use in penile implant and other urologic surgery.

B. Prior Art Background

In penile implant surgery, the need to dilate the corpora cavernosa to receive an inflatable or other type of prosthetic implant has been long known. The purpose of the implant is to enable the patient to achieve penile erection after the patient has lost this ability through disease or otherwise. In the process of the surgical technique to implant the prosthesis, the corpora cavernosa must be opened, dilated, and the prosthetic device inserted in the corpora. Since the penis is flaccid during the operation, a needle and suture must be taken through the corpora and exit through the glans end of the corpora and through the glans in order to pull the generally cylindrical implant through the length of the corpora.

Prior art devices which have been developed to accomplish this technique include the device of Furlow. This device is used for carrying needle and suture to the glans through the corpora after a series of generally cylindrical dilators, which, in order of increasing size, are inserted and removed so that the next larger cylinder may be inserted. The corpora, or other such opening is thereby dilated by the insertion of each successively larger dilating cylinder. This technique has the severe disadvantage of abrading the interior tissues since dilation depends on squeezing successively larger rods into the opening and along the corpora. Because the corpora is spongy tissue, there is no assurance that the same passage would be opened each time a new dilating rod is inserted. False passages can be created, with additional trauma resulting.

Another device is the device of Kollman. This dilator includes a longitudinally split dilating shaft, the sections of which are separated by a screw-powered lever at the base of the sections. Because of the resistence which is exerted by the glans end of the corpora on the tips of the sections, such devices have been difficult to use with precision and are usually ineffective in fully dilating the glans end of the corpora.

Neither of the aforementioned prior art devices include the means for dilation and for delivering accurately to and through the glans a needle and suture. The inaccuracy of needle placement through the glans of a flaccid penis, which is often the case with use of the Furlow device, has caused the needle to exit the side of the penis, or off center of the glans and can enter the urethra, causing unnecessary tissue damage. Additionally, when the needle is carried to the glans end of the corpora by Furlow's device, the needle rests loosely in a slot in the end of the largest cylindrical dilator to be used. If the needle is not to be passed through the glans before withdrawing the device, the needle can slip out and be lost in the corpora as the device is withdrawn.

C. Summary of the Invention

The invention includes a unitary variable dilator with longitudinally split sections radially separable from each other and a tapered or wedge-shaped inner member for positively and accurately separating the sections with means for securely holding an instrument at the point end of the inner member. The dilator is expanded radially by inserting the wedge-shaped inner member between the sections. A minimum of abrasion of the interior of the corpora is caused by this dilator because there is no multiple inserting and removing of different size dilators of the prior art. Another advantage of the present invention is the high degree of stability in positioning of the glans and accurate penetration thereof by the needle and suture in order to pull the implant therethrough. The inner sides of the dilator have cooperating grooves or slots along their length designed to receive the inner member as it is slid along the predetermined path between the split dilator sections to achieve radial expansion.

One embodiment of the invention includes markings indicating depth of penetration along the side of the dilator and markings along the inner member to indicate degree of dilation and position within the corpora of the instrument held by the inner member.

BRIEF DESCRIPTION OF THE DRAWINGS

FIG. 1 is a side elevation view of the preferred embodiment of the invention.

FIG. 2 is a side elevation view of the inner member.

FIG. 3 is a top plan view of the inner member.

FIG. 4 is a cross-sectional view of the inner member taken along 4—4 of FIG. 2.

FIG. 5 is a perspective view of the dilator showing the sections radially separated.

DESCRIPTION OF THE PREFERRED EMBODIMENT

Figure 6:
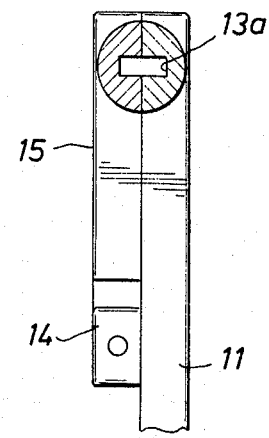
FIGS. 6, 7 and 8 are cross-sectional views along 5—5 of FIG. 1 progressively showing the dilator with its sections together, partially radially separated by the inner member, and fully separated by the inner member.

Referring now to the drawings, the dilator in FIG. 1 is generally designated by the numeral 10 having a handle portion (11) and a barrel portion (12). As can be seen in FIG. 5, barrel (12) is split longitudinally into two sections (13) and has therealong the reference markings (23). Sections (13) are mounted for movement away from each other by a hinge (14). Hinge (14) is securely mounted on handle (11). A support (15) connects each section (13) to hinge (14). The length of support (15) can be varied to determine the maximum separation between sections (13), and in the embodiment shown, supports (15) are in length about 2 to 4 times the diameter of section (13).

Figure 9:
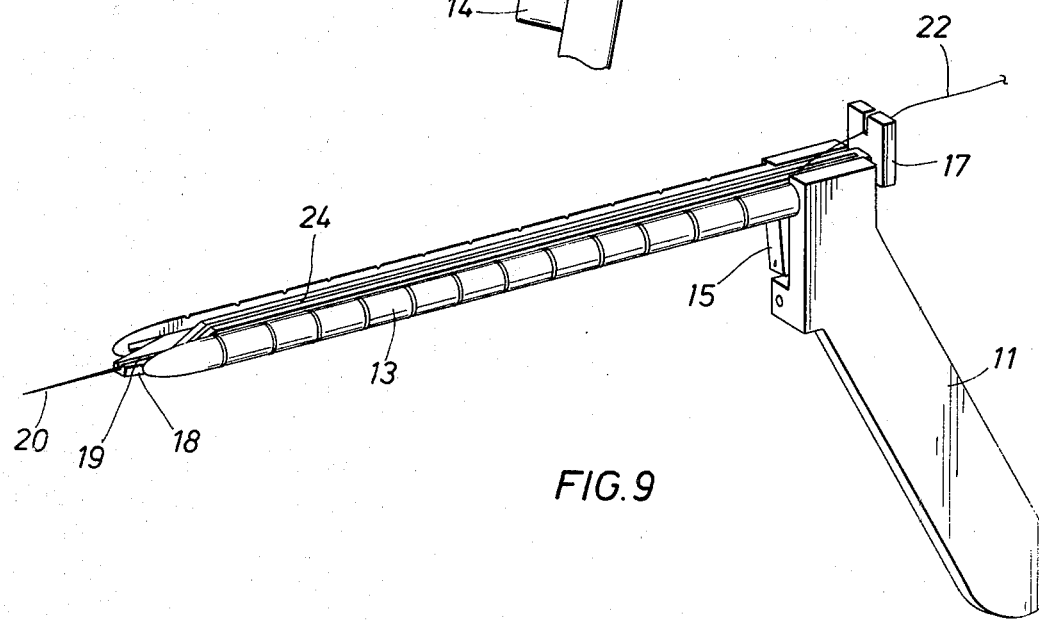
FIG. 9 is a perspective view of the dilator with inner member inserted and carrying a needle in its forwardmost portion.

Referring now to FIGS. 2 and 3, the inner member (16) is shown. Inner member (16) has at the rearwardmost portion thereof a perpendicular portion (17) for grasping by the user. Along the tip (18) of the inner member (16), a narrowed channel (19) is shown for frictionally engaging an instrument such as a needle (20) (FIG. 9). Narrowed channel (19) may be of whatever width necessary to frictionally engage the needle (20). Narrowed channel (19) is merely an extension of widened channel (24) of sufficiently narrow size to grasp the needle (20). Channel (19) or other such engaging means may be utilized to mount other useful instruments such as arthroscopes or other viewing devices. Inner member (16) may also have along its length the reference markings (21) for determining the degree of insertion of inner member (16) between sections (13) and, therefore, the degree of separation of sections (13).

In operation, dilator (12) with sections (13) in radially closed position is grasped by the handle (11) and inserted through an incision in a portion of the corpora cavernosa near the base end of the penis. The surgeon determines how far into the corpora dilator (12) should be inserted and markings (23) on barrel (12) signal to the surgeon to what extent barrel (12) has been inserted.

Figure 7:
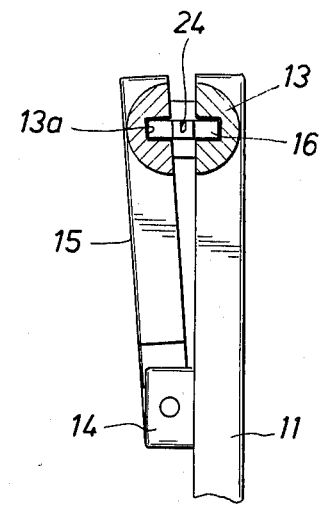
Figure 8:
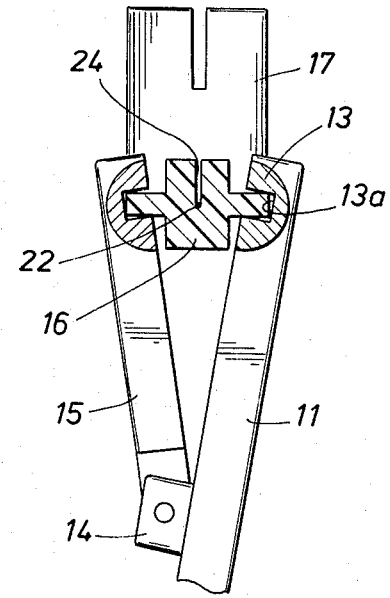

When barrel (12) has been inserted into the corpora to the desired position, inner member (16) is inserted tip (18) first into slots (13a). As inner member (16) is guided into slots (13a) to a greater extent, sections (13) are urged apart by the wedge-shaped forward portion of inner member (16). FIGS. 6, 7 and 8 show the increasing radial separation of sections (13) as the inner member (16) moves inside the corpora toward the forward tip of dilator (10) in the glans end of the penis within slots (13a). As sections (13) separate, proper dilation of the corpora is achieved and the glans is held steady by the separated ends of sections (13).

As inner member (16) slides along slots (13a) and dilates the corpora, inspection of the interior of the corpora may be made by a viewing instrument (not shown) mounted on tip (18). As shown in FIG. 9, channel (19) carries a needle (20) and suture (22) along the interior of the dilated corpora to the glans and thereof. The glans has been slightly stretched and stabilized at the ends of separated sections (13) and the needle can be pushed accurately and positively through that portion of the glans adjacent the end of the corpora.

Needle (20) is then disengaged from channel (19) and pulled through the glans. The dilator (10) is then withdrawn from the incision, leaving suture (22) running substantially the length of the corpora. The end of suture (22) projecting from the incision is connected to an implant (not shown). Suture (22) is then drawn through the glans, bringing along the implant through the incision to substantially fill the corpora. The suture is then removed from the implant and accessories are added to the implant at the base end thereof to inflate the implant or otherwise assist in operation of the prosthetic device when an erection is desired.

As may be seen in light of the specification, the word unitary as applied to the present dilator indicates a single instrument as opposed to techniques requiring multiple devices in the prior art. No multiple insertions of dilators of various sizes is required when the present invention is utilized.

Further modification and alternative embodiments of the apparatus of the invention will be apparent to those skilled in the art in view of this description. Accordingly, this description is to be construed as illustrative only and is for the purpose of teaching those skilled in the art the manner of carrying out the invention. It is to be understood that the form of the invention herewith shown and described is to be taken as the presently preferred embodiment.

I claim:

1. In apparatus for assisting in penile implant surgery, the combination comprising:
    a handle for said apparatus;
    a unitary dilator supported by said handle, said dilator being split longitudinally along the full length thereof in at least two radially separable sections; and
    means for uniformly and positively separating said sections along substantially the entire length thereof and for securely holding and carrying an instrument along a predetermined path from one longitudinal end of said dilator to the other longitudinal end of said dilator.

2. The apparatus as claimed in claim 1, wherein:
    said separating means takes the form of a wedge.

3. The apparatus as claimed in claim 2, wherein:
    said dilator sections are semi-circular in cross-section having slots to receive said separating means along the inner portions thereof; and
    said separating means has complimentary protrusions to fit said slots.

4. In apparatus for assisting in penile surgery, the combination comprising:
    an elongated dilator having a generally conical portion and longitudinal sections radially separable from each other;
    an inner member having a generally tapered portion adapted for insertion between said sections to cause said sections to be separated radially from each other;
    means for frictionally engaging an instrument mounted adjacent the point end of said inner member; and,
    a handle supporting said sections in a manner to permit outward radial movement of said sections.

* * * * *